United States Patent
Pekarske

(10) Patent No.: US 11,004,322 B2
(45) Date of Patent: May 11, 2021

(54) SYSTEMS AND METHODS FOR ADJUSTING MEDICAL DEVICE BEHAVIOR

(71) Applicant: GENERAL ELECTRIC COMPANY, Schenectady, NY (US)

(72) Inventor: Matthew Richard Pekarske, Grafton, WI (US)

(73) Assignee: General Electric Company, Schenectady, NY (US)

( * ) Notice: Subject to any disclaimer, the term of this patent is extended or adjusted under 35 U.S.C. 154(b) by 279 days.

(21) Appl. No.: 16/041,662

(22) Filed: Jul. 20, 2018

(65) Prior Publication Data

US 2020/0027328 A1    Jan. 23, 2020

(51) Int. Cl.
| | |
|---|---|
| *A61B 5/00* | (2006.01) |
| *G08B 21/04* | (2006.01) |
| *A61B 5/0205* | (2006.01) |
| *A61B 5/0245* | (2006.01) |
| *A61B 5/145* | (2006.01) |
| *A61B 5/01* | (2006.01) |
| *A61B 5/0402* | (2006.01) |

(Continued)

(52) U.S. Cl.
CPC ........ *G08B 21/0453* (2013.01); *A61B 5/0022* (2013.01); *A61B 5/0245* (2013.01); *A61B 5/02055* (2013.01); *A61B 5/721* (2013.01); *A61B 5/746* (2013.01); *A61B 5/01* (2013.01); *A61B 5/021* (2013.01); *A61B 5/02438* (2013.01); *A61B 5/04015* (2013.01); *A61B 5/04023* (2013.01); *A61B 5/11* (2013.01); *A61B 5/14542* (2013.01); *A61B 5/742* (2013.01); *A61B 2562/0219* (2013.01); *G08B 21/0446* (2013.01)

(58) Field of Classification Search
CPC ....... A61B 5/00; A61B 5/0205; A61B 5/0245; A61B 5/746; A61B 5/0022; A61B 5/0402; A61B 5/02055; A61B 5/0816; A61B 5/721; A61B 5/14542; A61B 2562/0219; A61B 5/11; A61B 5/04015; A61B 2560/0271; A61B 5/02438; A61B 5/01; A61B 5/742; A61B 5/021; A61B 2562/0257; A61B 5/04023; G08B 21/04; G08B 21/0453; G08B 21/0446
See application file for complete search history.

(56) References Cited

U.S. PATENT DOCUMENTS

| | | |
|---|---|---|
| 7,238,159 B2 | 7/2007 | Banet et al. |
| 8,077,143 B2 | 12/2011 | Panabaker et al. |

(Continued)

OTHER PUBLICATIONS

US 9,753,636 B2, 09/2017, Ban et al. (withdrawn)

(Continued)

*Primary Examiner* — Eric J Messersmith

(57) ABSTRACT

System and methods are disclosed for adjusting behavior of a medical device. An exemplary method includes monitoring physiological data of a patient and determining whether the medical device is stationary or in motion based on detection by a proximity sensor or a motion sensor. The method further includes displaying the monitored physiological data in a first display mode in response to determining that the medical device is stationary and displaying the monitored physiological data in a second display mode in response to determining that the medical device is in motion. The second display mode is simplified comparing to the first display mode.

17 Claims, 4 Drawing Sheets

(51) Int. Cl.
    *A61B 5/04*         (2006.01)
    *A61B 5/11*         (2006.01)
    *A61B 5/024*       (2006.01)
    *A61B 5/021*       (2006.01)

(56) References Cited

U.S. PATENT DOCUMENTS

| | | |
|---|---|---|
| 8,180,440 B2 | 5/2012 | McCombie et al. |
| 8,591,411 B2 | 11/2013 | Banet et al. |
| 9,566,007 B2 | 2/2017 | McCombie et al. |
| 9,792,033 B2 | 10/2017 | Ban et al. |
| 10,470,020 B2 * | 11/2019 | Lockenour ............... H04W 4/14 |
| 2007/0271115 A1 * | 11/2007 | Baldus .................... G06F 19/00 705/2 |
| 2012/0274554 A1 | 11/2012 | Kinoshita et al. |
| 2017/0258401 A1 * | 9/2017 | Volpe ................... A61B 5/6805 |
| 2018/0226141 A1 * | 8/2018 | Slepian ................. G16H 10/60 |

OTHER PUBLICATIONS

Khan et al., A Detailed Algorithm for Vital Sign Monitoring of a Stationary/Non-Stationary Human through IR-UWB Radar, PMCID: PMC5336124, https://www.ncbi.nlm.nih.gov/pmciarticles/PMC5336124/, last viewed Jul. 20, 2018, 20 pages.

\* cited by examiner

SYSTEMS AND METHODS FOR ADJUSTING MEDICAL DEVICE BEHAVIOR

TECHNICAL FIELD

This disclosure relates to systems and methods for adjusting behavior of medical devices, more specifically, wireless patient monitors, based on motion.

BACKGROUND

Wireless patient monitors are widely used in care delivery areas such as patient monitoring, fetal monitoring, and rehabilitation services. Physiological conditions of patients or fetuses, such as electrocardiogram (ECG), blood pressure, temperature, heart rate, oxygen saturation, etc., can be monitored and transmitted by the wireless patient monitor to a remote processing system. During a typical wirelessly monitored patient stay, the acuity level of the patient may vary which necessitates the patient to move from one care area to another care area. For example, a patient may enter an emergency department, be taken back to an imaging department, moved to a surgery preparation area, then into the operating room, transferred to a step-down unit, and then ultimately discharged. When the patient is transported, the medical devices used for monitoring the patient's health go along with the patient. The medical devices can move around, be jostled, or bounce a little as the patient bed is moved by a clinician.

When the patient is stationary, the clinician generally has more time to review the monitored physiological data that is present on a display of the monitoring device, such as waveforms, trends, historical data, and so on. On the other hand, during transport of the patient, the motion makes it hard for the clinician to read smaller fonts, numbers, and physiological waveforms. Furthermore, at a patient transport corridor, wireless connectivity is not always adequate so the monitoring device may raise additional technical alarms for poor connectivity. These alarms could be a nuisance to clinicians remotely monitoring the patient as they are likely already aware the patient is in transport from one ward to another.

SUMMARY

In one embodiment, the present disclosure provides a medical device for monitoring a patient. The medical device comprises a display configured to display monitored physiological data of the patient, a proximity sensor configured to detect proximity of the medical device to one or more targets positioned in a healthcare environment, and a controller communicably connected to the display and the proximity sensor. This controller is configured to determine whether the medical device is stationary or in motion based on detection by the proximity sensor, make the display present the monitored physiological data in a first display mode in response to determining that the medical device is stationary, and make the display present the monitored physiological data in a second display mode in response to determining that the medical device is in motion. The second display mode is different from the first display mode.

In another embodiment, the present disclosure provides a wireless patient monitor, which comprises one or more medical sensors configured to monitor physiological data of a patient, a display configured to display the monitored physiological data of the patient, a wireless communication interface configured to transmit the monitored physiological data to a remote server, a motion sensor configured to detect motion status of the wireless patient monitor, and a controller communicably connected to the one or more medical sensors, display, wireless communication interface, and motion sensor. The controller is configured to determine whether the wireless patient monitor is stationary or in motion based on detection by the motion sensor, make the display present the monitored physiological data in a first display mode in response to determining that the wireless patient monitor is stationary, and make the display present the monitored physiological data in a second display mode in response to determining that the wireless patient monitor is in motion. The second display mode is different from the first display mode.

In yet another embodiment, the present disclosure provides a method for adjusting behavior of a medical device. The method comprises monitoring physiological data of a patient, determining whether the medical device is stationary or in motion based on detection by a sensor, displaying the monitored physiological data in a first display mode in response to determining that the medical device is stationary, and displaying the monitored physiological data in a second display mode in response to determining that the medical device is in motion. The second display mode is different from the first display mode.

BRIEF DESCRIPTION OF THE DRAWINGS

Various aspects of this disclosure may be better understood upon reading the following detailed description and upon reference to the drawings in which.

Figure 1:
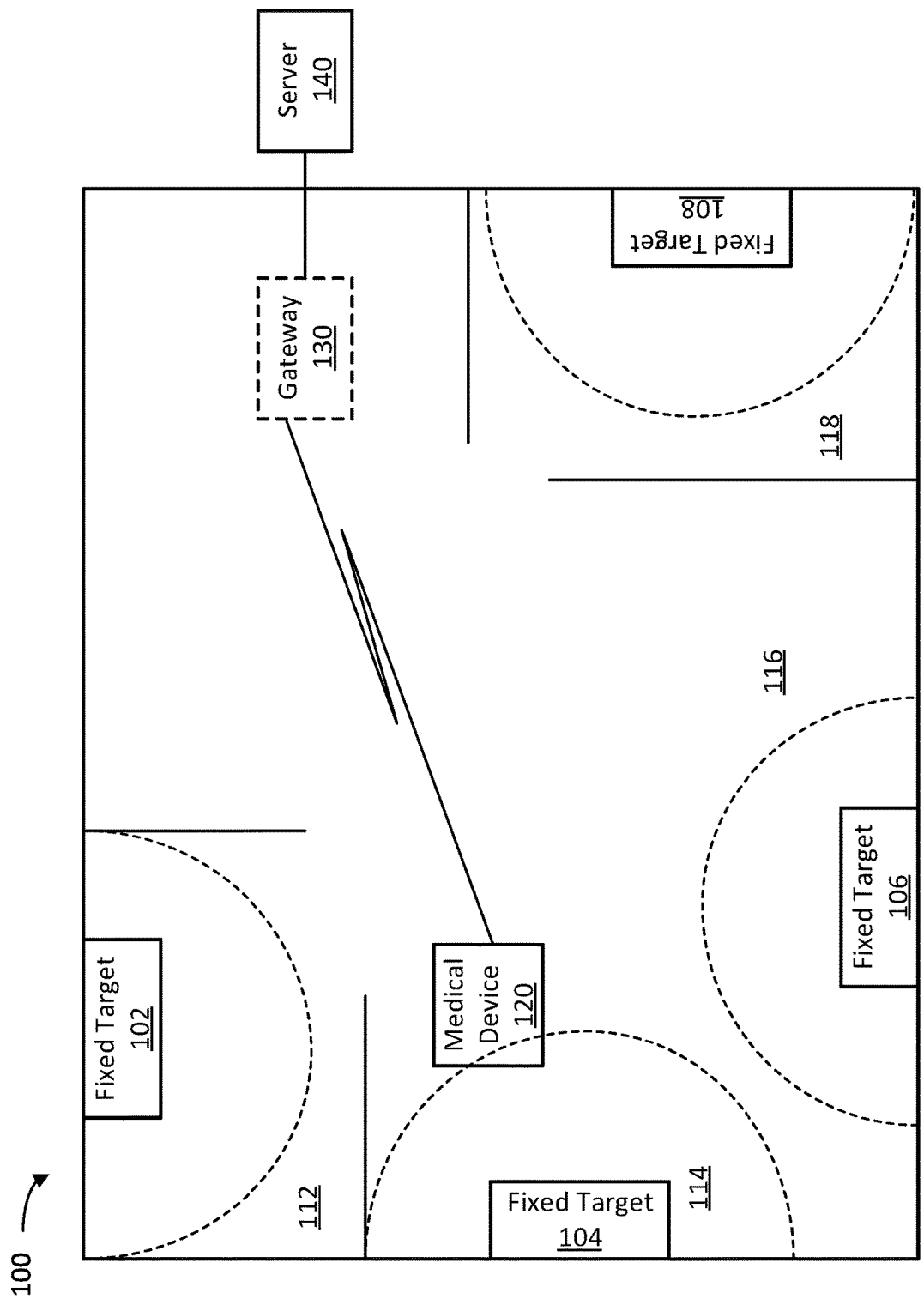
FIG. 1 is a schematic diagram of a healthcare environment in which a medical device operates, in accordance with an exemplary embodiment.

The drawings illustrate specific aspects of the described systems and methods for adjusting medical device behavior. Together with the following description, the drawings demonstrate and explain the principles of the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

One or more specific embodiments of the present disclosure are described below in order to provide a thorough understanding. These described embodiments are only examples of systems and methods for adjusting medical device behavior. The skilled artisan will understand that specific details described in the embodiments can be modified when being placed into practice without deviating the spirit of the present disclosure.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

Referring to the figures generally, the present disclosure is to provide systems and methods for adjusting behavior of a medical device, and more specifically, a wireless patient monitor. An exemplary method detects automatically whether the medical device is in motion (e.g., goes along with a patient in transport) or stationary via proximity-based or motion-based technology. If the medical device is in motion, the monitored physiological data of the patient displayed at the medical device is simplified comparing to the displayed information in stationary. For example, the medical device may display waveforms (e.g., ECG waveform, respiration waveform), trends, historical data in detail in the stationary state while display only numerical values of important parameters (e.g., heart rate, blood oxygenation, respiration rate) in large font in the mobile state. This becomes particularly valuable for devices with small displays. In addition, if the medical device is in motion, technical alarms regarding poor wireless connectivity are delayed and/or suppressed.

Technical solutions disclosed herein can increase the usability of medical devices during patient transport and reduce technical alarms associated with poor wireless network connectivity typically raised during patient transport. When the patient is being transported from one care area to another, detailed view is not always needed or necessary. By detecting the mobile state, the medical device can change physiological data display to be more readable by the clinician. Simply displaying numerical values of critical parameters instead of detailed information, especially on medical devices with small displays (e.g., bedside monitors), would be enough for the clinician to ensure the patient is stable during transport. In addition, by detecting the mobile state, the medical device can reduce the numbers of or delay the time to raise technical alarms associated with poor wireless network connectivity which is often observed in, for example, patient transport corridors.

Referring to FIG. 1, a schematic diagram of a healthcare environment 100 (e.g., a hospital, clinic, doctor's office, etc.) in which a medical device 120 operates is shown, in accordance with an exemplary embodiment. The healthcare environment 100 includes various areas 112, 114, 116, and 118 defined by walls and/or functions. For example, the area 112 is an operating room, area 118 is a recovery room, and areas 114 and 116 are corridors connecting 112 and 118.

One or more fixed targets are positioned (e.g., affixed to a wall and/or other structure) in one or more areas 112-118 of the environment 100. As shown in FIG. 1, for example, a fixed target 102 is positioned in area 112, fixed target 104 in area 114, fixed target 106 in area 116, and fixed target 108 in area 118. Each of the fixed targets 102-108 communicates or broadcasts beacon signals for a covered range (e.g., ranges shown with dashed lines in FIG. 1), using near field communication (NFC), radio frequency identification (RFID), Bluetooth, iBeacon, or the like. The medical device 120 includes a proximity sensor (e.g., RFID reader, Bluetooth radio) configured to detect the beacon signals transmitted from the targets, which will be described in detail below with reference to FIG. 2. In operation, each of the fixed targets 102-108 may continually or periodically (e.g., every second, 2 seconds, 3 seconds, etc.) communicate or broadcast beacon signals. The medical device 120 may continually or periodically look for beacon signals from the targets. When the medical device 120 is within the covered range of a fixed target, the medical device 120 detects the beacon signals regarding the respective target. As shown in FIG. 1, medical device 120 can detect the fixed target 104 when moving into the ranged covered by the fixed target 104.

In some embodiments, a beacon signal from a fixed target includes target identifying information which may be a unique identifier of the respective fixed target, such as a MAC address, serial number, alphanumeric signature, etc. The beacon signal may include additional or alternative information, such as a time stamp (e.g., Jul. 18, 2018, 9:10:04 am), signal strength level, frequency channel, and so on.

It should be noted that any proximity-based sensor technology can be utilized herein, such as NFC, RFID, Bluetooth, iBeacon, and so on. Proximity-based technology relies on a sensor being able to detect a target ranging from as close as few millimeters (mm) to over several meters (m) of separation. Moreover, various proximity-based technologies may be employed in a single implementation of the medical device 120. In other words, this disclosure is not limited to a particular proximity-based technology as certain physiological measurements and subsequent device actions may desire different ranges of detection (e.g., a patient in transport passing through a RFID checkpoint between wards or passing by multiple Bluetooth beacons).

In some embodiments, the medical device 120 is a wireless patient monitor that communicates with a remote server 140 through wireless communication links (e.g., antennas, access points). In some embodiments, communication with the server 140 can be routed through a gateway 130 and/or other edge device. The server 140 may process the information (e.g., monitored physiological data, wireless connectivity, motion status, etc.) received from the medical device 120 or send the information to a central station (not shown in the present figures) for processing/viewing via, for example, a dedicated network interface (e.g., dedicated Ethernet). The wireless communication link may employ various wireless communication protocols used with antennas, access point, or similar infrastructure, such as Bluetooth, Bluetooth Low Energy (BLE), ZigBee, Wi-Fi, infrared, ultrasound, and so on.

At the server 140 or central station, monitored physiological data for multiple patients may be displayed simultaneously. In addition, the server 140 or central station may generate various types of alarms based on data received from the medical device 120. For example, patient physiological alarms are triggered if alarm limits for the respective physiological parameter are exceeded, or certain data patterns are detected. Technical alarms can be generated if network connectivity is poor. In some embodiments, alarms include audible noises and/or flashing lights at the medical device 120. In some embodiments, the server 140 or central station generates alarm notifications for sending to mobile devices (e.g., pagers, PDAs, mobile phones) of caregivers via, for example, an alert or alarm notification system (e.g., ASCOM alarm notification system).

It should be understood that the configuration as shown in FIG. 1 is for illustration not for limitation. Any appropriate changes to, for example, fixed targets configuration, network configuration, etc., can be made. For example, in alternative embodiments, the medical device 120 may include a wireless tag (i.e., as the proximity sensor) that communicates or broadcasts beacon signals while the one or more fixed targets positioned in the environment 100 look for the beacon signals. When the medical device 120 is within the range covered by a fixed target, the respective target may detect the beacon signals from the medical device 120 and send an acknowledgement message to the medical device 120. Upon receiving the acknowledgement message, the medical device 120 is notified of the proximity to the respective fixed target.

Figure 2:
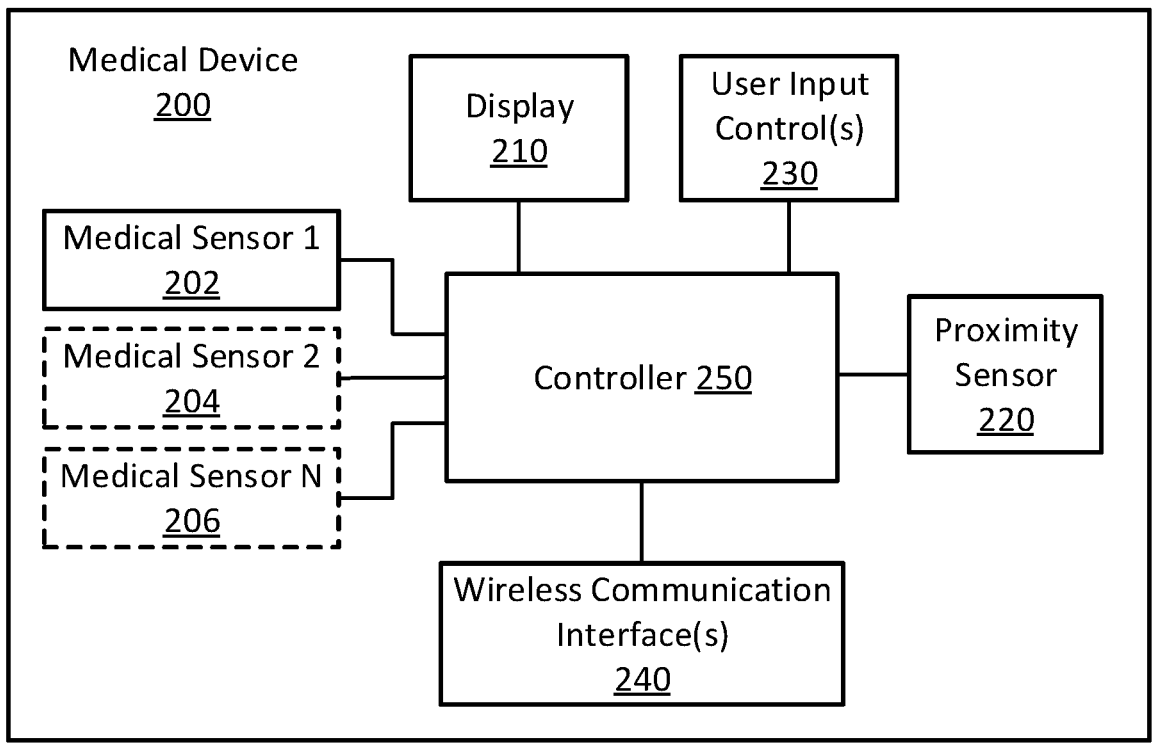
FIG. 2 is a block diagram of a medical device which can be used in FIG. 1, in accordance with an exemplary embodiment.

Referring to FIG. 2, a block diagram of a medical device 200 which can be used in FIG. 1 (i.e., corresponds to medical device 120 in FIG. 1) is shown, in accordance with an exemplary embodiment. In some embodiments, the medical device 200 is a bedside wireless patient monitor, which moves along with a patient bed and monitors one or more physiological parameters for the patient. The medical device 200 may include one or more medical sensors 202, 204, and 206, including, for example, ECG electrodes for sensing ECG, scalp electrodes for sensing electroencephalograph (EEG), a blood pressure cuff for sensing non-invasive blood pressure (NIBP), a fingertip pulse oximetry sensor for sensing peripheral oxygen saturation (SpO2), a temperature sensor for sensing patient temperature, and so on. Each of the medical sensors 202-206 measures one or more physiological parameters from the patient and communicates measurement information to a controller 250. In some embodiments, the medical sensors 202-206 are not part of the medical device 200 but independent devices. The medical device 200 includes interfaces (e.g., slots, wireless transceivers) for receiving measurement information from the medical sensors 202-206.

Figure 3A:
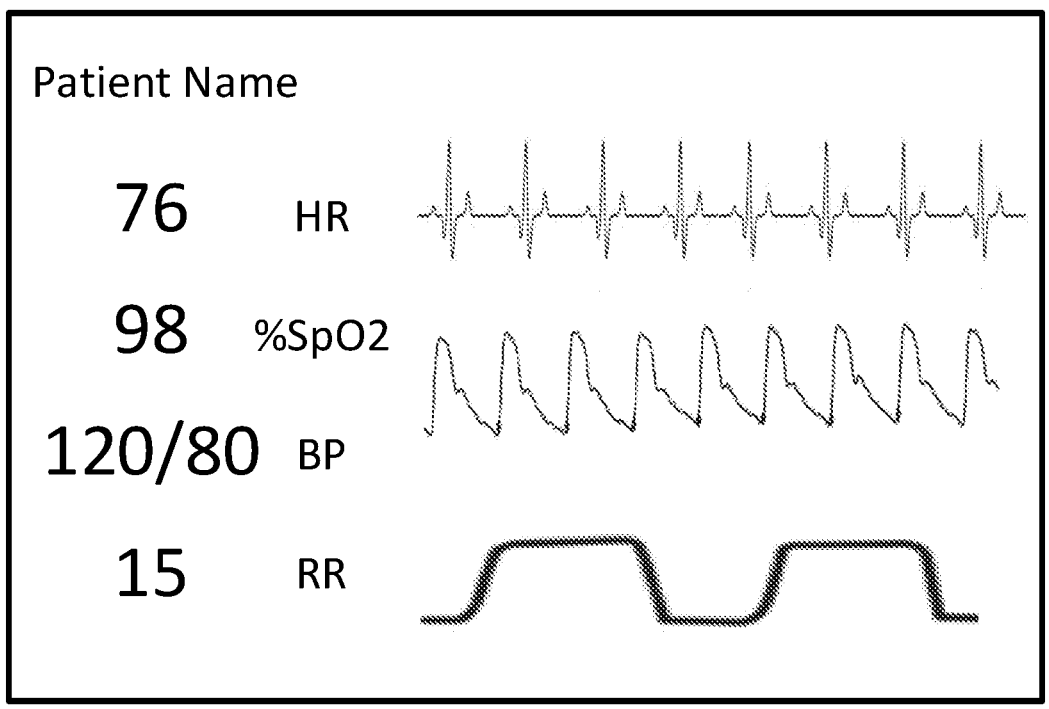
FIG. 3A shows a first display mode of a medical device, in accordance with an exemplary embodiment.
Figure 3B:
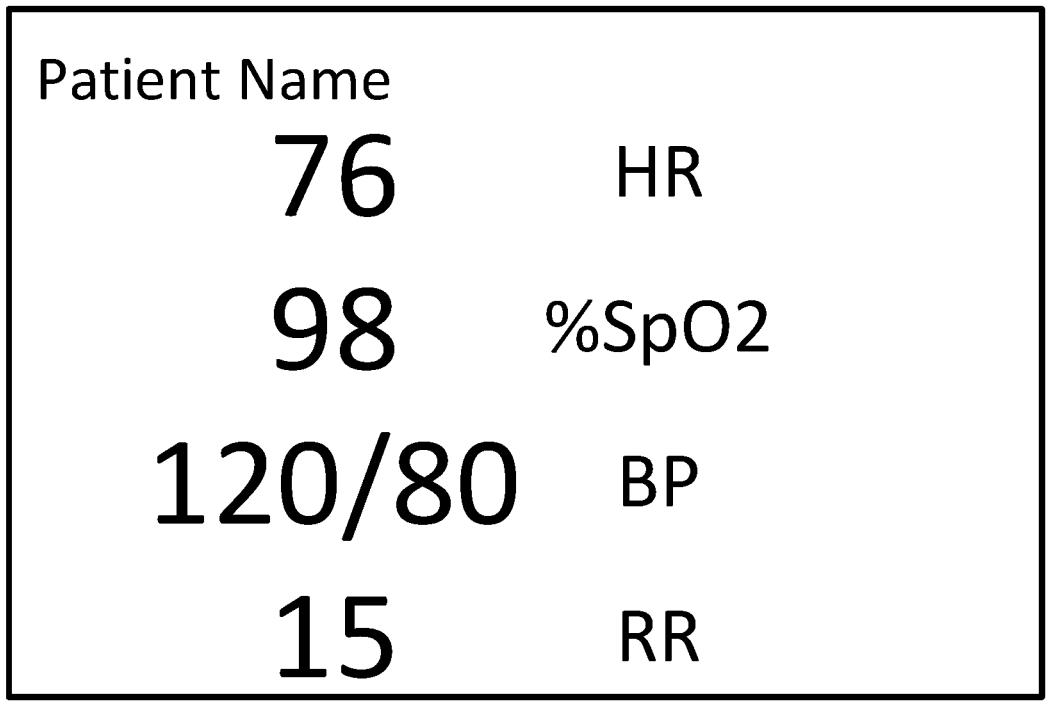
FIG. 3B shows a second display mode of the medical device, in accordance with an exemplary embodiment.

The medical device 200 also includes a display 210 for displaying the physiological data of the patient monitored by the medical sensors 202-206. In some embodiments, the display 210 includes a screen (e.g., touchscreen). The display 210 may be configured by the controller 250 to display the monitored physiological data in different modes. Referring to FIGS. 3A and 3B, two display modes are shown, in accordance with an exemplary embodiment. FIG. 3A illustrates a first display mode which displays both numerical values and waveforms of the monitored physiological data (e.g., ECG, SpO2, blood pressure, respiration rate). FIG. 3B illustrates a second display mode which is a simplified version of the first mode and displays only the numerical values of the monitored physiological data with larger fonts. It should be understood that the first and second display modes as shown in FIGS. 3A and 3B are for illustration, not for limitation. The controller 250 may configure the display 210 to present the monitored physiological data in any appropriate ways, such as including trends, historical data, charts, more, fewer, or different parameters with any appropriate color, font, style, etc.

Referring back to FIG. 2, the medical device 200 further includes a proximity sensor 220 configured to detect beacon signals from the fixed targets 102-108 in the environment 100, using any appropriate proximity-based sensor technologies, such as NFC, RFID, Bluetooth, iBeacon, and so on. As discussed above with reference to FIG. 1, when the medical device 120 is within the predefined range of a fixed target, the target sensor 220 detects the beacon signals regarding the respective target and communicates the information to the controller 250.

The medical device 200 includes one or more user input control(s) 250 which facilitates control of the medical device 200 by a user, such as activating/deactivating the medical device 200, configurating the medical device 200, etc. The user input control(s) 250 may include hardware (keyboard, button switch), software (interactive graphical user interface), middleware, or any appropriate combination thereof.

The one or more wireless communication interface(s) 240 of the medical device 200 facilitates the communication between the medical device 200 and a remote server (e.g., server 140 of FIG. 1). The controller 250 may transmits monitored patient physiological data, detected target information, wireless connectivity, as well as other data to the server via the wireless communication interface(s) 240, which may employ various wireless communication protocols used with antennas, access point, or similar infrastructure, such as Bluetooth, Bluetooth Low Energy (BLE), ZigBee, Wi-Fi, infrared, ultrasound, and so on.

The controller 250 controls operations for the medical device 200 including target detection, patient monitoring, data communication, timing, memory operation, etc. In some embodiments, the controller 250 includes a processor (e.g., a central processing unit (CPU)), memory, radio frequency (RF) core for radio communication, sensor control, peripheral control, and so on. The processor executes instructions stored in the memory to facilitate programming, testing, and/or operation of the medical device 200. In some embodiments, the memory stores information of the fixed targets associated with the areas where they are positioned. For example, the memory may store a lookup table which associates the identifying information of the fixed target 102 with area 112 (operating room), fixed target 104 with area 114 (corridor), fixed target 106 with area 116 (corridor), and fixed target 108 with area 118 (recovery room). In some embodiments, the information of the fixed targets associated with the areas where they are positioned is not stored at medical device 200, but at the remote server or central station. The medical device 200 communicates the received beacon signals to the server or central station, the server or central station identifies the associated fixed target and communicates back to the medical device 200.

Upon detecting proximity to a fixed target, the controller 250 determines whether the medical device 200 is stationary or in motion based on the respective fixed target. For example, if the beacon signal indicates that the medical device 200 is in a range covered by the fixed target 102 (or the fixed target 108), the controller 250 may determine that the medical device 200 is stationary in the operating room (or the recovery room). If the beacon signal indicates that the medical device is in a range covered by the fixed target 104 (or the fixed target 106), the controller 250 may determine that the medical device 200 is in motion, going along with the patient to pass the corridor(s). As another example, fixed targets are positioned at only the corridor(s) but not the rooms. The controller 250 may determine that the medical device is stationary if no beacon signal is detected and determine that the medical device is in motion upon detecting any beacon signal. It should be understood that the above approaches are described as non-limiting examples. Any appropriate methods can be used to determine the stationary or mobile status of the medical device 200 based on detection of proximity, such as using signal strength levels, real time location system (RTLS), etc.

The controller 250 may then configure the display 210 based on the stationary or mobile state of the medical device 200. For example, the controller 250 may instruct the display 210 to present the monitored physiological data in the first mode (e.g., shown in FIG. 3A) if the medical device 200 is determined to be stationary, or instruct the display 210 to present in the second mode (e.g., shown in FIG. 3B) if the medical device 200 is determined to be in motion.

In addition, in some embodiments, the controller 250 may suppress or delay technical alarms regarding poor wireless connectivity in response to determining the medical device 200 is in motion. In other embodiments, the controller 250 may communicate to the server or central station that the medical device 200 is in motion and the server or central station may suppress or delay the technical alarms of poor network connectivity from its end.

It should be understood that the medical device 200 as shown in FIG. 2 is for illustration, not for limitation. A medical device may include more, fewer, and/or different components. For example, in alternative embodiments, the medical device 200 may include a wireless tag as the proximity sensor 220. The wireless tag communicates or broadcasts beacon signals while the one or more fixed targets positioned in the environment 100 look for the beacon signals. When the medical device 200 is within the range covered by a fixed target, the respective target may detect the beacon signals from the medical device 200 and send an acknowledgement message to the medical device 200. Upon receiving the acknowledgement message, the medical device 200 is notified of the proximity to the respective fixed target.

Figure 4:
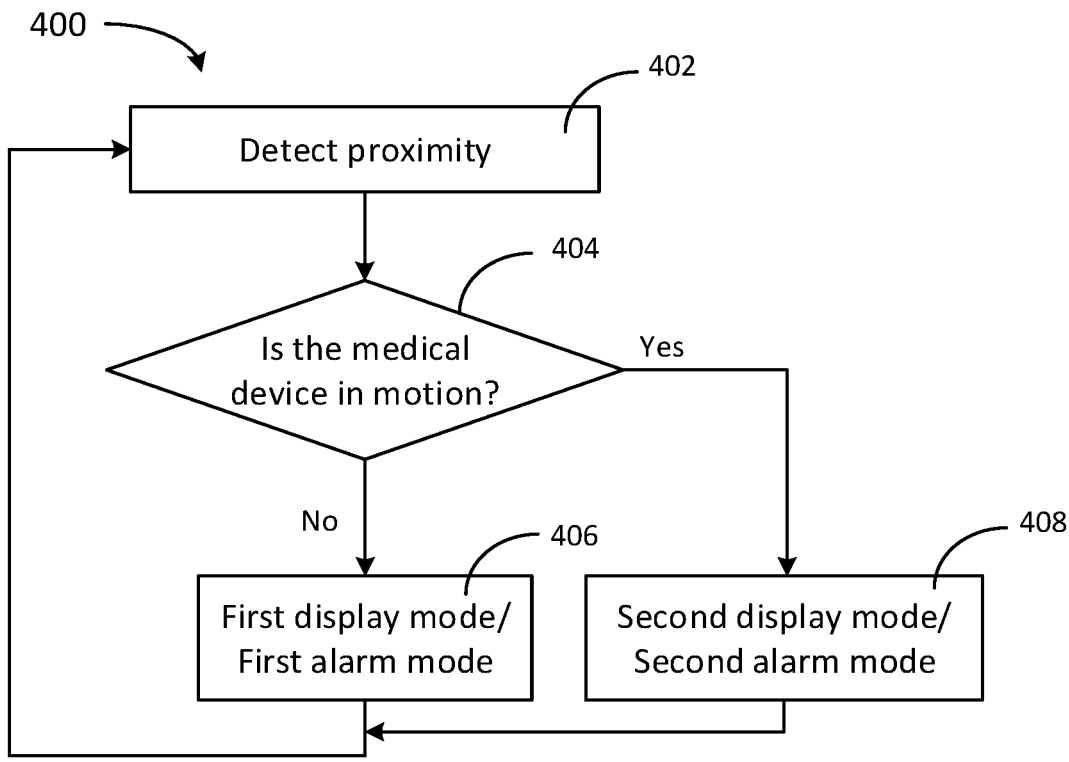
FIG. 4 is a flow chart of a method for adjusting medical device behavior, in accordance with an exemplary embodiment.

Referring to FIG. 4, a flow chart 400 of a method for adjusting medical device behavior is shown, in accordance with an exemplary embodiment. The method can be executed by the medical device 200 in FIG. 2. At an operation 402, proximity of the medical device 200 to fixed targets positioned in a healthcare environment is detected. In some embodiments, the medical device 200 may continually or periodically (e.g., every second, 2 seconds, 3 seconds, etc.) detect beacon signals transmitted by fixed targets positioned in various areas of the healthcare environment, using any appropriate proximity-based sensor technologies, such as NFC, RFID, Bluetooth, iBeacon, and so on. When the medical device 200 is within the predefined range of a fixed target, the beacon signal regarding the respective target is detected. The beacon signal includes target identifying information which may be a unique identifier of the respective fixed target such as a MAC address, serial number, alphanumeric signature, etc. The beacon signal may include additional or alternative information, such as a time stamp, signal strength level, frequency channel, and so on.

In alternative embodiments, the medical device 200 continually or periodically communicates or broadcasts beacon signals while the one or more fixed targets positioned in the environment 100 look for the beacon signals. When the medical device 200 is within the range covered by a fixed target, the respective target may detect the beacon signals from the medical device 200 and send an acknowledgement message to the medical device 200. Upon receiving the acknowledgement message, the medical device 200 is notified of the proximity to the respective fixed target.

At an operation 404, it is determined whether the medical device 200 is in motion based on the proximity detected at 402. In some embodiments, the medical device 200 stores information of the fixed targets associated with the areas where they are positioned. If the beacon signal indicates that the medical device 200 is in a range covered by certain fixed target (e.g., target 102 or 108) at a room, the medical device 200 is determined to be stationary. If the beacon signal indicates that the medical device is in a range covered by certain fixed target (e.g., target 102 or 106) at the corridor, the medical device is determined to be in motion, i.e., going along with the patient to pass the corridor. In some embodiments, fixed targets are positioned at only the corridor(s) but not the rooms. The medical device 200 is determined to be stationary if no beacon signal is detected while determined to be in motion upon detecting any beacon signal.

In some embodiments, the information of the fixed targets associated with the areas where they are positioned is stored at the remote server or central station. The medical device 200 queries the server or central station to determine the stationary or mobile state of itself. It should be understood that the above approaches are described as non-limiting examples. Any appropriate operations can be used to determine the stationary or mobile status of the medical device 200 based on detection of proximity, such as using signal strength levels, real time location system (RTLS), etc.

At an operation 406, the medical device 200 displays the monitored physiological data with a first display mode and/or the alarm mode is set as a first alarm mode, if the medical device 200 is determined to be stationary at 404. For example, the medical device 200 displays the monitored physiological data as shown in FIG. 3A, which includes displaying detailed information such as numerical values, waveforms, trends, historical data, etc. In addition, the medical device 200 raises technical alarms as soon as wireless connectivity is poor in the first alarm mode.

At an operation 408, the medical device 200 displays the monitored physiological data with a second display mode and/or the alarm mode is set as second alarm mode, if the medical device 200 is determined to be in motion at 404. For example, the medical device 200 displays the monitored physiological data as shown in FIG. 3B, which may include displaying only numerical values with larger fonts. In addition, the medical device 200 suppresses or delay technical alarms relating to poor wireless connectivity in the second alarm mode. Furthermore, the medical device 200 may communicate to the server or central station that the medical device 200 is in motion and the server or central station may suppress or delay the technical alarms relating to poor wireless connectivity from its end.

It should be understood that the process as shown in FIG. 4 is for illustration not for limitation. An appropriate process may include more, fewer, or different operations than those shown in FIG. 4.

Figure 5:
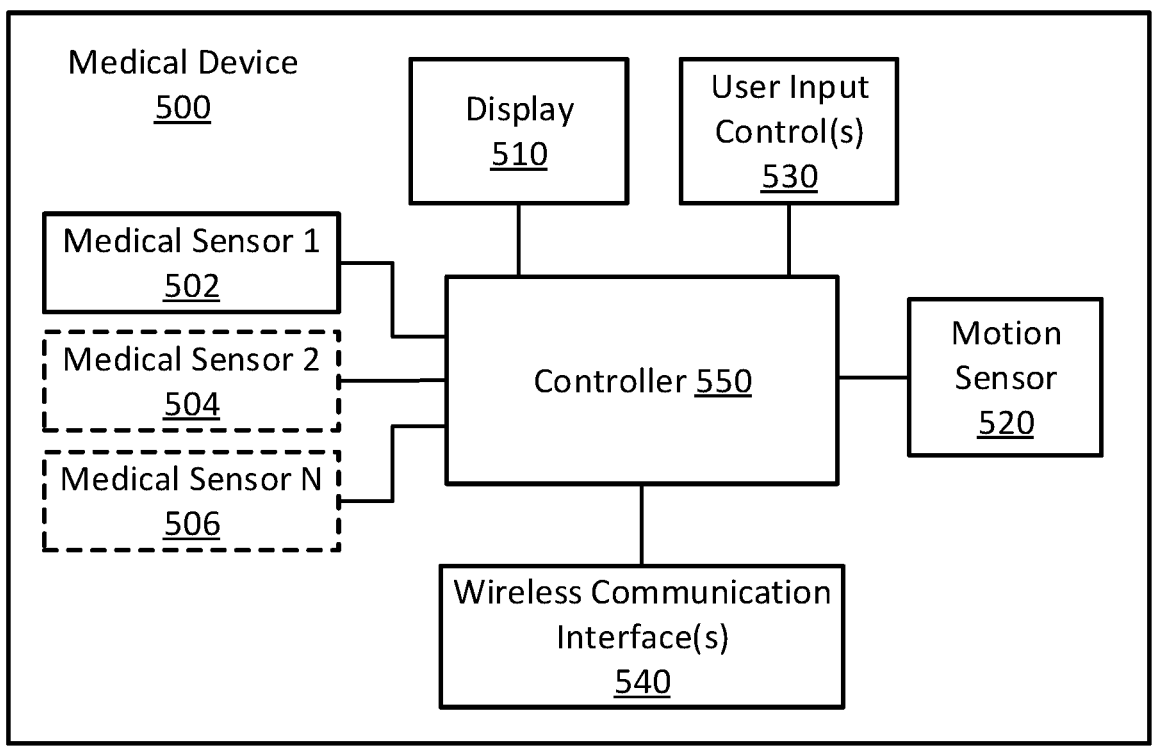
FIG. 5 is a block diagram of a medical device which can be used in FIG. 1, in accordance with another exemplary embodiment.

Referring to FIG. 5, a block diagram of a medical device 500 which can be used in FIG. 1 (e.g., corresponding to medical device 120 in FIG. 1) is shown, in accordance with another exemplary embodiment. Components of the medical device 500 may be the same as or similar to corresponding components of the medical device 200 in FIG. 2 except that the medical 500 includes a motion sensor 520 rather than the proximity sensor 220. The motion sensor 520 may be an accelerometer, gyroscope sensor, or any other appropriate type of motion sensor. The motion sensor 520 may continually detect the stationary or mobile state of the medical device 500 and communicate the detection to the controller 550.

Figure 6:
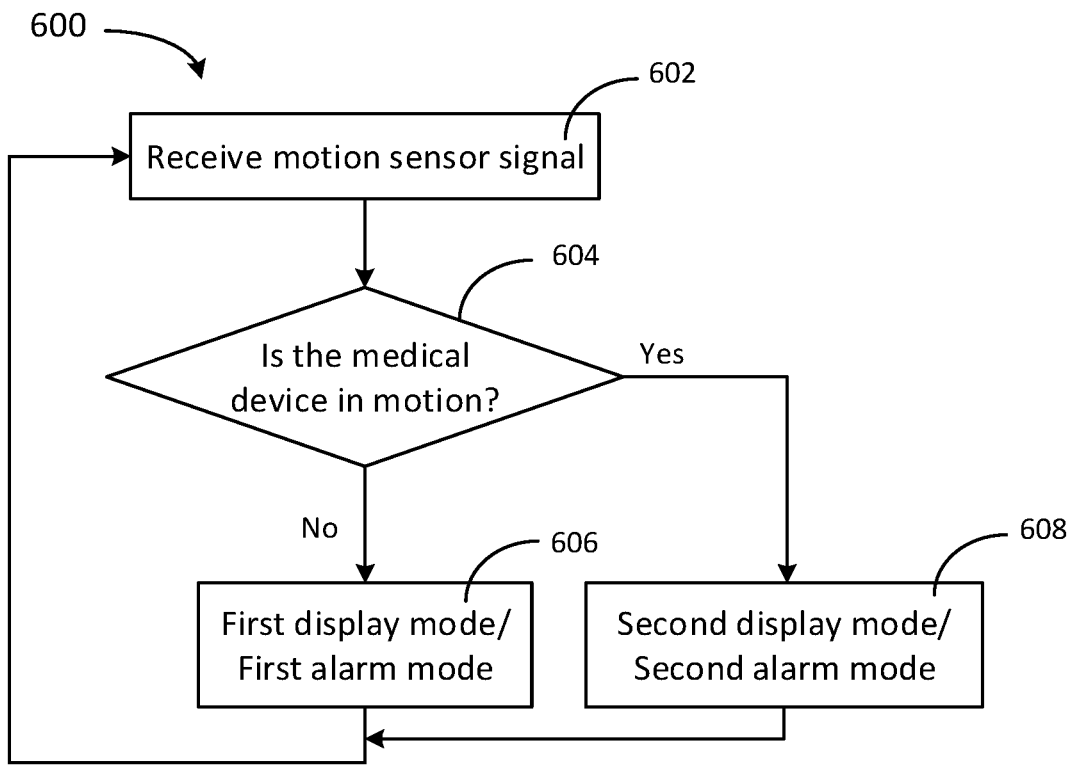
FIG. 6 is a flow chart of a method for adjusting medical device behavior, in accordance with another exemplary embodiment.

Referring to FIG. 6, a flow chart of a method 600 for adjusting medical device behavior is shown, in accordance with another exemplary embodiment. The method can be executed by the medical device 500 in FIG. 5. Operations of the method 600 may be the same as or similar to corresponding operations of method 400 shown in FIG. 4 except that at operation 602, motion sensor signal rather than proximity is received and at operation 604, the medical device is determined to be stationary or mobile based on the received motion sensor signal.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

What is claimed is:

1. A medical device for monitoring a patient, wherein the medical device comprises:
    a display configured to display monitored physiological data of the patient;
    a proximity sensor configured to detect proximity of the medical device to one or more targets positioned in a healthcare environment; and
    a controller communicably connected to the display and the proximity sensor and configured to:
        determine whether the medical device is stationary or in motion based on detection by the proximity sensor;
        suppress or delay a technical alarm regarding wireless connectivity of the medical device in response to determining that the medical device is in motion based at least in part on identifying information of the one or more targets within the healthcare environment;
        make the display present the monitored physiological data in a first display mode in response to determining that the medical device is stationary; and
        make the display present the monitored physiological data in a second display mode in response to determining that the medical device is in motion, wherein the second display mode is different from the first display mode.

2. The medical device of claim 1, wherein determining whether the medical device is stationary or in motion comprises:
    determining that the medical device is in motion in response to detecting proximity to a target positioned at a corridor of the healthcare environment.

3. The medical device of claim 1, wherein detecting proximity of the medical device to one or more targets comprises detecting beacon signals transmitted from the one or more targets, and the beacon signals comprise identifying information that identifies a respective target.

4. The medical device of claim 3, wherein determining whether the medical device is stationary or in motion comprises:
    determining that the medical device is in motion if the identifying information indicates the respective target positioned at a corridor of the healthcare environment.

5. The medical device of claim 1, wherein the second display mode is simplified comparing to the first display mode.

6. The medical device of claim 1, wherein the first display mode displays both numerical values and waveforms for the monitored physiological data, and the second display mode displays only the numerical values.

7. The medical device of claim 1, further comprising:
    one or more medical sensors configured to monitor at least one of ECG, SpO2, blood pressure, respiration, and temperature of the patient.

8. The medical device of claim 1, further comprising:
    one or more medical sensor interfaces configured to receive the monitored physiological data from one or more medical sensors.

9. The medical device of claim 1, further comprising a wireless communication interface configured to facilitate communication of the medical device with a remote server.

10. The medical device of claim 1, wherein the controller is to generate a lookup table to store the identifying information for the one or more target areas in the healthcare environment.

11. A wireless patient monitor comprising:
    one or more medical sensors configured to monitor physiological data of a patient;
    a display configured to display the monitored physiological data of the patient;
    a wireless communication interface configured to transmit the monitored physiological data to a remote server;
    a motion sensor configured to detect motion status of the wireless patient monitor; and
    a controller communicably connected to the one or more medical sensors, display, wireless communication interface, and motion sensor and configured to:
        determine whether the wireless patient monitor is stationary or in motion based on detection by the motion sensor;
        suppress or delay a technical alarm regarding wireless connectivity of the wireless patient monitor in response to determining that the wireless patient monitor is in motion based at least in part on identifying information of one or more targets in an area;
        make the display present the monitored physiological data in a first display mode in response to determining that the wireless patient monitor is stationary; and
        make the display present the monitored physiological data in a second display mode in response to determining that the wireless patient monitor is in motion, wherein the second display mode is different from the first display mode.

12. The wireless patient monitor of claim 11, wherein the first display mode displays both numerical values and waveforms for the monitored physiological data, and the second display mode displays only the numerical values.

13. A method for adjusting behavior of a medical device, the method comprising:
    monitoring, by the medical device, physiological data of a patient;
    determining, by the medical device, whether the medical device is stationary or in motion based on detection by a sensor;
    suppressing or delaying a technical alarm regarding wireless connectivity of the medical device in response to determining that the medical device is in motion based at least in part on identifying information of one or more fixed targets in an area;

displaying, by the medical device, the monitored physiological data in a first display mode in response to determining that the medical device is stationary; and displaying, by the medical device, the monitored physiological data in a second display mode in response to determining that the medical device is in motion, wherein the second display mode is different from the first display mode.

14. The method of claim 13, wherein the monitored physiological data comprises at least one of ECG, SpO2, blood pressure, respiration, and temperature.

15. The method of claim 13, wherein the sensor is a motion sensor.

16. The method of claim 13, wherein the second display mode is simplified comparing to the first display mode.

17. The method of claim 13, wherein the first display mode displays both numerical values and waveforms for the monitored physiological data, and the second display mode displays only the numerical values.

* * * * *